(12) United States Patent
Nogawa et al.

(10) Patent No.: US 8,192,447 B2
(45) Date of Patent: Jun. 5, 2012

(54) MEDICAL DEVICE AND USING METHOD THEREOF

(75) Inventors: Atsuhiko Nogawa, Kanagawa-ken (JP); Fumihisa Hirose, Tokyo (JP); Yasushi Kinoshita, Fujinomiya (JP); Shigeki Ariura, Kanagawa-ken (JP); Hiroshi Shiono, Kanagawa-ken (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 1227 days.

(21) Appl. No.: 11/861,043

(22) Filed: Sep. 25, 2007

(65) Prior Publication Data

US 2008/0255404 A1    Oct. 16, 2008

(30) Foreign Application Priority Data

Sep. 29, 2006  (JP) ................................ 2006-268628

(51) Int. Cl.
   *A61B 17/10*   (2006.01)
   *A61B 18/04*   (2006.01)
   *A61M 37/00*   (2006.01)

(52) U.S. Cl. .............. 606/139; 606/27; 600/12

(58) Field of Classification Search .......... 606/75, 606/108, 139, 142, 153, 219, 1, 27, 32, 40; 600/9, 11, 12, 104; 227/175.1, 179.1; 607/122
See application file for complete search history.

(56) References Cited

U.S. PATENT DOCUMENTS

| | | | |
|---|---|---|---|
| 5,330,486 A * | 7/1994 | Wilk | 606/139 |
| 5,702,412 A | 12/1997 | Popov et al. | |
| 6,010,498 A * | 1/2000 | Guglielmi | 606/108 |
| 6,068,637 A | 5/2000 | Popov et al. | |
| 6,542,766 B2 | 4/2003 | Hall et al. | |
| 6,638,297 B1 * | 10/2003 | Huitema | 606/219 |
| 6,840,246 B2 | 1/2005 | Downing | |
| 6,890,353 B2 | 5/2005 | Cohn et al. | |
| 6,985,776 B2 * | 1/2006 | Kane et al. | 607/122 |
| 7,287,682 B1 * | 10/2007 | Ezzat et al. | 227/175.1 |

FOREIGN PATENT DOCUMENTS

| | | |
|---|---|---|
| JP | 11-514263 A | 12/1999 |
| WO | WO 97/12555 A2 | 4/1997 |

OTHER PUBLICATIONS

Official Action dated Mar. 1, 2011, issued by the Japanese Patent Office in corresponding Japanese Patent Application No. 2006-268628, and English language translation of the Japanese Official Action.

* cited by examiner

*Primary Examiner* — Julian Woo
(74) *Attorney, Agent, or Firm* — Buchanan Ingersoll & Rooney PC

(57) ABSTRACT

Disclosed herein is a medical device including: a positioning catheter to be inserted into a blood vessel in the vicinity of an affected region; a treatment catheter to be inserted to reach the affected region; and attracting means provided at respective predetermined positions of both the catheters to apply a magnetic force in a direction of attracting each other; wherein the magnetic force of the attracting means restricts floating of the treatment catheter.

15 Claims, 7 Drawing Sheets

MEDICAL DEVICE AND USING METHOD THEREOF

CROSS REFERENCES TO RELATED APPLICATIONS

The present invention contains subject matter related to Japanese Patent Application JP 2006-268628 filed in the Japan Patent Office on Sep. 29, 2006, the entire contents of which being incorporated herein by reference.

BACKGROUND OF THE INVENTION

1. Field of the Invention

The present invention relates to a medical device and using method thereof to cure a valve body of a human heart or the like.

2. Description of the Related Art

One of recent problematic heart diseases is such that blood does not flow normally because of incomplete closing of a heart valve body. Examples of such heart diseases include mitral insufficiency in which blood flows back from the left ventricle into the left atrium because of the incomplete closing of a mitral valve and aortic insufficiency in which blood flows back from the aorta into the left ventricle because of incomplete closing of the aortic valve.

These diseases are curable by narrowing an opening portion formed in the heart valve body. Examples of such treatments include a drug treatment and an open-heart operation. In order to cure a heart disease caused by structure only by a drug treatment, it is difficult to adjust the dosage of drugs and there is a problem with fast-acting property. Therefore, these diseases are cured by an open-heart operation. The permanent operation eliminates the risk of relapse though it is invasive. However, inclusively taking into account a risk resulting from the extracorporeal circulation of blood during the operation and the magnitude of invasion resulting from thoracotomy, it is desired to perform the operation through percutaneous catheterization which provides the same effect as that of the open-heart operation.

To meet the desire, the medical device described in U.S. Pat. No. 6,542,766 B2 (see abstract, columns 2 and 3, FIGS. 2A and 16, etc.) has been proposed recently. This medical device is used for treatment as below. A tubular magnetic elongate element is led to a heart using a catheter. A magnetic line is applied to the elongate element from outside so as to orient it in a predetermined direction. Thereafter, an electric current is applied from the magnetic elongate element to an affected area for removal or a drug solution is directly applied to the affected area.

U.S. Pat. No. 6,890,353 B2 (see abstract, etc.) discloses a device which sort of reinforces a mitral valve by implanting a tunnel member in the coronary vein of the heart.

U.S. Pat. No. 6,840,246 B2 (see abstract, etc.) discloses a device which is used to narrow an opening portion by sewing a mitral valve while visually observing the inside of the heart with an endoscope.

In the device disclosed in U.S. Pat. No. 6,542,766 B2, it is difficult to perform the following procedure. A procedure catheter is placed in constantly flowing blood as in the heart and a magnetic line is applied from outside to the procedure catheter to prohibit it from floating. In addition, the treatment using a treatment catheter is limited so that also the treatment has a problem in view of accuracy. In the device disclosed in U.S. Pat. No. 6,890,353 B2, since a foreign object is implanted in the blood vessel, it is probable to impede the smooth flow of the blood. In the device disclosed in U.S. Pat. No. 6,840,246 B2, since the inside of the heart is visually observed with an endoscope, a large amount of normal saline must be allowed to flow to ensure a range of view. However, despite this, it is probably not to perform the accurate visual observation.

SUMMARY OF THE INVENTION

It is an object of this invention to provide a medical device which has a simple configuration and which restricts floating of a treatment catheter even in blood flow to bring it into positional fixation, sufficiently ensures an assistant force needed to treat an affected area, and simplifies a correct treatment.

It is an object of this invention to provide a medical device that includes: a positioning catheter to be inserted into a blood vessel in the vicinity of an affected region; a treatment catheter to be inserted to reach the affected region; and attracting means provided at respective predetermined positions of both the catheters to apply a magnetic force in a direction of attracting each other; wherein the magnetic force of the attracting means restricts floating of the treatment catheter.

It is an object of this invention to provide a using method of the medical device restrict floating of a treatment catheter by a magnetic force of the attracting means, including the steps of: inserting a positioning catheter in a blood vessel close to an affected region; inserting the treating catheter to reach the affected region; and allowing both the catheters to attract each other by the attracting means which are provided at respective predetermined positions of both the catheters to apply a magnetic force.

In the present invention, the positioning catheter to be inserted into a blood vessel (a coronary vein) in the vicinity of an affected region and the treatment catheter to be inserted to reach the affected region are each provided with the attracting means for applying a magnetic force in a direction of attracting each other. The magnetic force can be applied to the positioning catheter from a position extremely close to the treatment catheter so that the treatment catheter can more forcibly be pulled to restrict the floating thereof. Thus, even if cure is performed under the condition where a quantity of blood flows, the treatment catheter will not be floated by the blood, which enhances the operability encountered when a predetermined procedure is carried out. In addition, the treatment can be performed easily and quickly, with a high degree of accuracy. In particular, the magnetic force is strengthened in inverse proportion to distance squared. If the magnetic adsorption force is used, it is necessary to reduce the distance therebetween as much as possible. For example, the distance between the coronary vein and the coronary artery in the heart is about 2.5 mm. The magnetic force applied between both the catheters at such a distance provides a fixation force stronger than that obtained by inducing the treatment catheter with a magnetic field outside a body or the heart.

The treatment catheter uses the magnetic force of the attracting means to take a position conforming to the positioning catheter; therefore, sort of an initial position is specified. Also in this point, the operability during the treatment is enhanced. In particular, if the procedure in which the treatment catheter punctures a valve body or the like is performed, the magnetic force attracting the treatment catheter assists force needed for the procedure. Also in this point, the high-accuracy, speeding-up, and facilitation of the treatment can be promoted.

If the clip member or the anchor member is used as the inosculating means for narrowing the opening portion of the mitral valve or aortic valve, it is necessary to ensure force adapted to pass the valve body through the narrowed opening portion. If the positioning catheter forcibly pulls the treatment catheter at close range, the magnetic force assists the force needed for the puncture of the clip member or anchor member. Further, the treatment catheter which serves to hold such inosculating means can positionally be fixed. In this way, the procedure is performed in this fixed state, which can assist the procedure itself of the inosculating means.

If the positioning catheter and treatment catheter are each provided with the markers at its leading end, the positions of both the catheters can be identified, whereby the high-accuracy, speeding-up, and facilitation of the treatment can further be promoted.

DETAILED DESCRIPTION OF THE PREFERRED EMBODIMENTS

Preferred embodiments of the present invention will hereinafter be described in detail with reference to the accompanying drawings.

Figure 1:
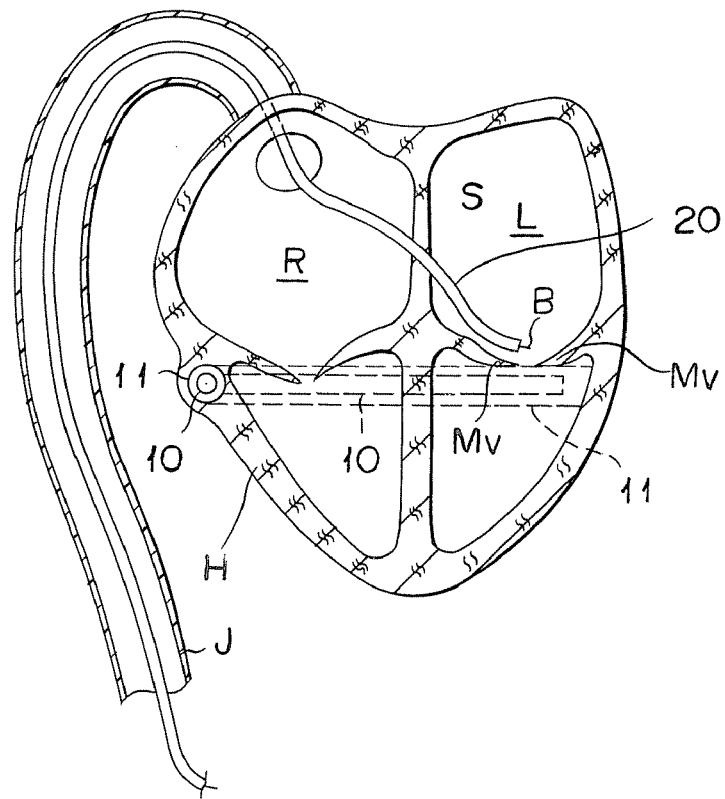
FIG. 1 is a schematic cross-sectional view illustrating usage of a medical device according to an embodiment of the present invention.

As shown in FIG. 1, a medical device of the present embodiment is used to cure mitral insufficiency and adapted to reduce the area of a mitral orifice O surrounded by a mitral valve Mv of a heart H.

The medical device generally includes a positioning catheter 10, a treatment catheter 20 and an adsorption section 30. The positioning catheter 10 is disposed in a coronary vein (or a coronary artery) close to the mitral valve Mv which is an affected region. The treatment catheter 20 is inserted very close to the affected region. The adsorption section 30 is attached to the tips of the positioning catheter 10 and treatment catheter 20 to apply a magnetic force in the direction of attracting each other. The magnetic force of the adsorption section 30 pulls the treatment catheter 20 toward the positioning catheter 10 to restrict floating of the treatment catheter 20. Thus, the position of the treatment catheter 20 is brought into a fixedly stationary state, thereby achieving the smoothness, speeding-up, facilitation and accuracy of treatment.

The further detailed description is made. The positioning catheter 10 is a thin tube inserted into a blood vessel, e.g. a coronary vein 11 located close to the mitral valve Mv which is the affected region. The positioning catheter 10 is formed of a material such as vinyl chloride, PCB (polychlorobiphenyl), polypropylene, polyimide, or the like so as to have a usual outer diameter of about 0.9 mm. An insertion method involves inserting the positioning catheter 10 into an inferior vena cava of a femur and allowing it to reach a coronary vein 11 present along the outer circumference of the heart H from the outside. Although any method may be adopted, the tip of the positioning catheter 10 will be implanted in the coronary vein 11.

Figure 2:
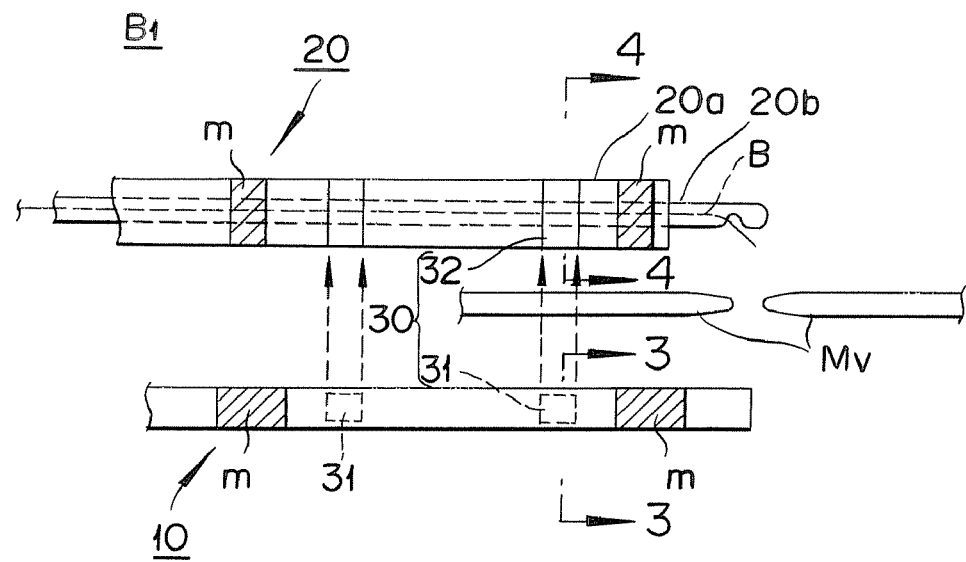
FIG. 2 is a schematic cross-sectional view of a main portion of the embodiment.

Referring to FIG. 2, the positioning catheter 10 is provided at its leading end with a plurality of permanent magnets 31 axially spaced apart from each other, which serves as the adsorption section 30. The plurality of permanent magnets 31 are provided to be axially spaced apart from each other so that the treatment catheter 20 described later can be superposed on, be commensurate with, attracted to and held by the linear positioning catheter 10. Consequently, floating of the treatment catheter 20 can be restricted more forcibly. In particular, a magnetic force is strengthened in inverse proportion to distance squared. Therefore, if the distance between the positioning catheter 10 and the treatment catheter 20 is reduced as much as possible, a fixation force can be provided which is stronger than that obtained by inducing the treatment catheter with a magnetic field outside a body or the heart. The distance between the coronary vein 11 and the inside of the atrium is about 2.5 mm. With this distance, if a magnetic force is applied between the catheters 10, 20, an extremely intense magnetic force can be applied. Consequently, a fixation force can be provided which is stronger than that obtained by inducing the treatment catheter from outside a body or the heart with a magnetic field.

Figure 3:
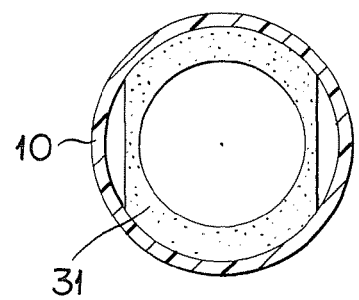
FIG. 3 is a cross-sectional view taken along line 3-3 of FIG. 2.

Referring to FIG. 3, the permanent magnet 31 is formed of a tubular hollow body received in the catheter 10 for the purpose of weight reduction. However, the permanent magnet 31 may be formed of a solid body. Alternatively, a thin circular permanent magnet may be stuck on the external surface of the catheter 10 in some situations.

Figure 4:
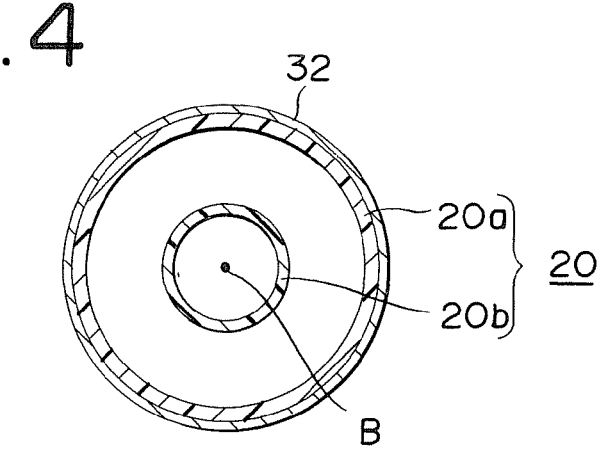
FIG. 4 is a cross-sectional view taken along line 4-4 of FIG. 2.

On the other hand, as shown in FIGS. 2 and 4, the treatment catheter 20 includes a guide catheter 20a, a procedure catheter 20b inserted into the guide catheter 20b, and inosculating section B provided in the procedure catheter 20b. These catheters 20a, 20b are formed of the same material as that of the positioning catheter 10. Although not restrictive, for example, the outer diameter of the guide catheter 20a is about 2 mm to 4 mm and the outer diameter of the procedure catheter 20b is about 0.5 mm to 2 mm.

In the embodiment, the procedure catheter 20b is loosely fitted into the guide catheter 20a; therefore, it can freely be moved forward or backward or operatively turned in the guide catheter 20a so as to enhance the procedure operability. Thus, the accuracy, smoothness, speeding-up, and facilitation of the treatment can be enabled.

As shown in FIG. 2, the guide catheter 20a is provided at its leading end with a plurality of to-be-attracted members 32 as the adsorption section 30 axially spaced apart from each other. The to-be-attracted member 32 is made of a metal material with magnetically attracted performance such as stainless steel. As shown in FIG. 4, a thin circular member stuck on the external surface of the guide catheter 20a is used as the to-be-attracted member 32. Preferably, the to-be-attracted member 32 is provided on the external surface of the guide catheter 20a in order to make it easy to be attracted by the magnetic force (broken line arrows in FIG. 2) of the permanent magnets 31. However, the to-be-attracted member 32 may be provided on the inner surface of or in a wall thickness portion of the guide catheter 20a.

Needless to say, the adsorption section 30 is not necessarily configured such that the positioning catheter 10 is provided with the permanent magnets 31 and the treatment catheter 20 is provided with the to-be-attracted member 32 and it may be configured vice versa. Specifically, the following examples are applicable.

Figure 5:
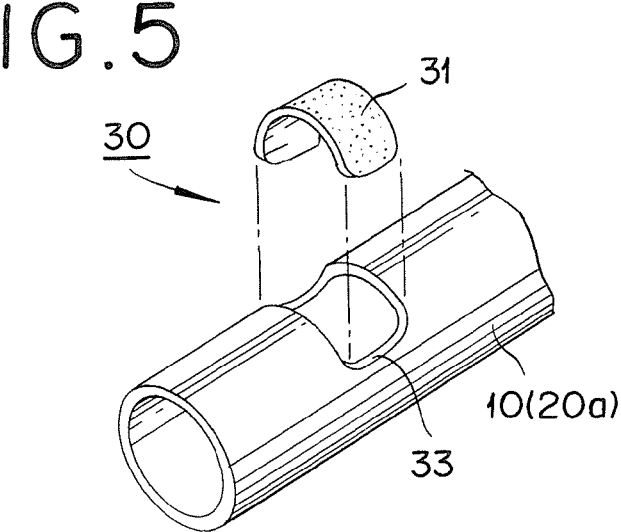
FIG. 5 is a schematic perspective view illustrating application example 1 of the adsorption section.

Application example 1 shown in FIG. 5 is configured such that a sheet-like permanent magnet 31 is fitted and bonded to a recessed portion 33 formed by partially removing the positioning catheter 10 or the guide catheter 20a.

Figure 6:
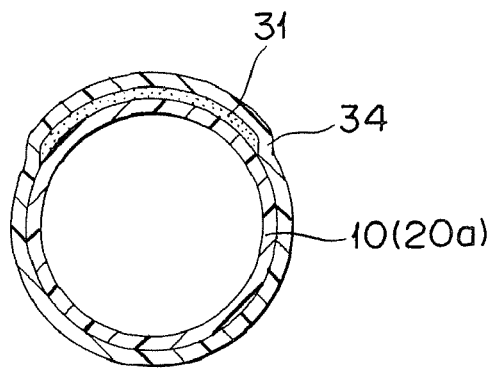
FIG. 6 is a schematic cross-sectional view of application example 2 of the adsorption section.

Application example 2 shown in FIG. 6 is configured such that a sheet-like permanent magnet 31 is placed on the surface of the positioning catheter 10 or guide catheter 20a and covered by a thin sheet 34.

Figure 7:
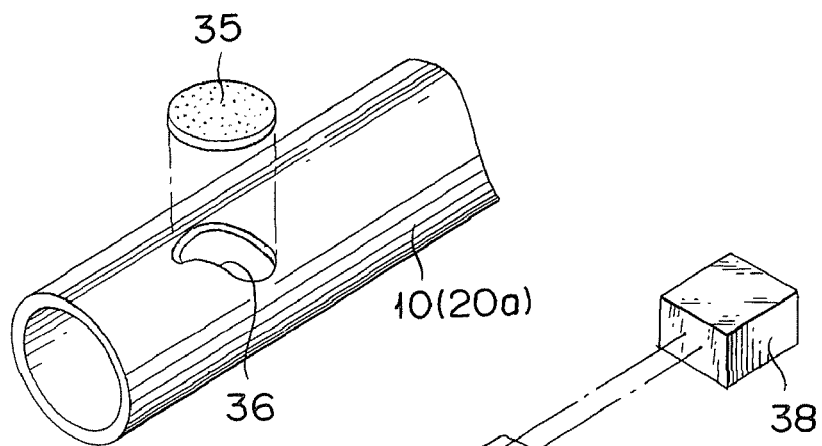
FIG. 7 is a schematic perspective view of application example 3 of the adsorption section.

Application example 3 shown in FIG. 7 is configured such that a so-called magnet chip 35 is buried in or bonded to a hole portion 36 bored in the catheter 10 or guide catheter 20a.

Figure 8:
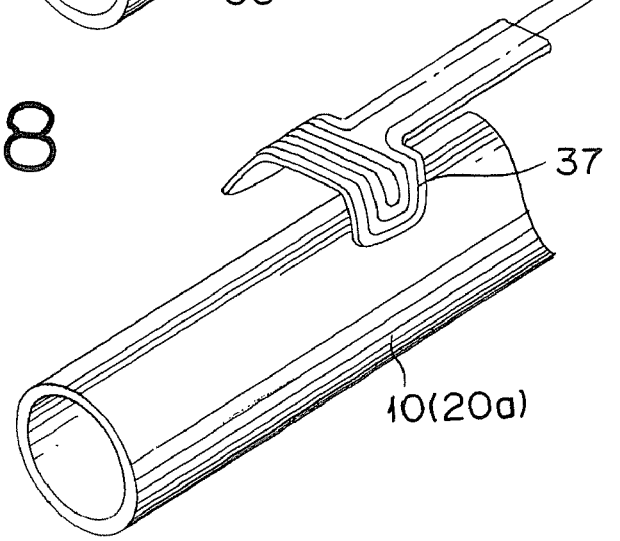
FIG. 8 is a schematic perspective view of application example 4 of the adsorption section.

Application example 4 shown in FIG. 8 is configured such that a flat formed induction coil 37 is bonded to the front surface of the positioning catheter 10 or guide catheter 20a and current-controlled by a control unit 38 from the outside. However, these adsorption sections 30 are only exemplary and the present invention is not limited to such an adsorption section 30.

The so-called markers m made of a radiopaque material (e.g. gold, silver, platinum, tungsten, palladium or the alloy thereof) is provided in the vicinities of the adsorption section 30 included in the positioning catheter 10 and treatment catheter 20. With such markers, the respective tips of the catheters 10, 20 can accurately be led to and implanted at a predetermined position in the coronary vein 11 close to the mitral valve Mv or at a position very close to the mitral valve Mv which is an affected region, while confirming the positions of the catheters 10, 20 in the living body.

In this way, the adsorption section 30 and the markers m are provided for each of the treatment catheter 20 and positioning catheter 10. The catheters 10, 20 can independently be inserted into a living body from different positions by an operator manipulating them. This can achieve the smoothness, speeding-up, facilitation and accuracy of the procedure.

Figure 9A:
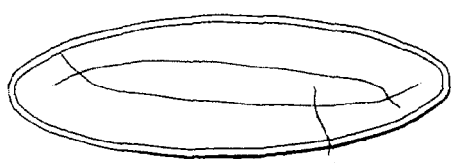
FIGS. 9A, 9B and 9C are schematic views of a main portion of the mitral valve, illustrating an abnormal state, a treatment state by inosculating section and a treatment completion state, respectively.
Figure 9B:
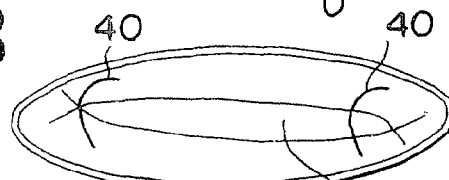
Figure 9C:
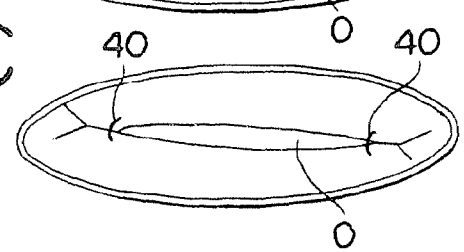

The inosculating section B provided in the treatment catheter 20 is used to reduce the area of the mitral orifice O surrounded by a mitral valve Mv. If normal, the mitral valve Mv is such that a pair of valve bodies is superposed with each other so as to allow blood to flow in one direction. If abnormal, the mitral valve Mv has a large opening portion O as shown in FIG. 9A. The mitral valve Mv is cured by inosculating both lateral portions of the opening portion O so as to come close to each other by use of line members 40, thereby making the opening portion O small as shown in FIG. 9C.

The following section can be used as the inosculating section B by way of examples.

Usage Example 1

The inosculating section B1 of usage example 1 includes the line member 40 inserted in the procedure catheter 20b and fracture section 41 (schematically shown in FIG. 10C) which fractures or cuts the line member 40 every predetermined length.

The line member 40 is made of a shape memory alloy so as to be extremely thin. After punctured the affected region, if the line member is fractured or cut by the fracture section 41, it functions as a loop-like clip member 40a which self-deforms arcuately. This clip member 40a self-deforms to narrow the opening portion O.

The fracture section 41 is composed of a remote-controllable scissors-like member. However any member will be applicable as long as it can fracture or cut the line member 40. If the line member 40 is preliminarily formed with weakened portions (not shown) such as notches every predetermined length, fracture can easily be done by the fracture section 41 and thus the procedure can smoothly be performed. However, it is not necessarily needed to use the fracture section in the present embodiment. For example, if the fracture section fractured every predetermined length is continuously inserted into the procedure catheter 20b, inosculation can be performed only by sequentially feeding the line member from the procedure catheter 20.

Figure 10A:
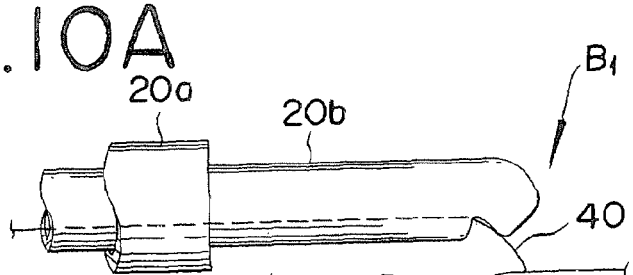
FIGS. 10A, 10B and 10C are schematic views illustrating usage example 1 of the inosculating section, FIG. 10A illustrating a state where the inosculating section punctures one of the mitral valves, FIG. 10B illustrating a state where the inosculating section punctures both the mitral valves, and FIG. 10C illustrating a state where the inosculation is complete.
Figure 10B:
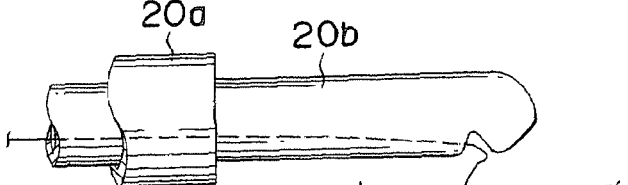
Figure 10C:
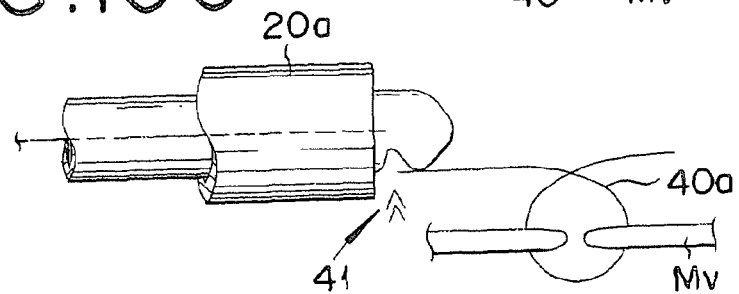
Figure 11:
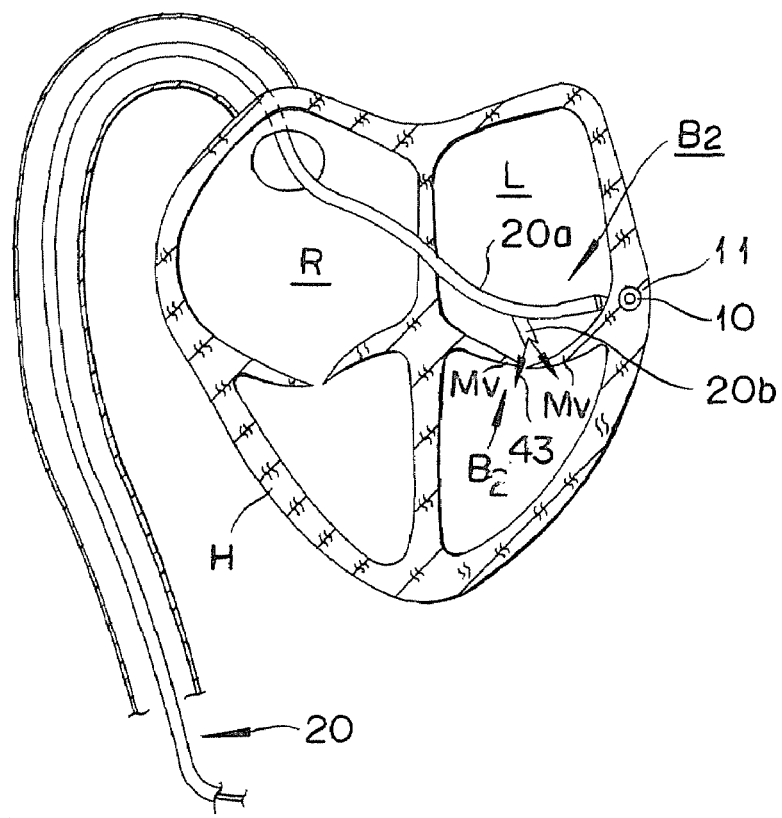
FIG. 11 is a schematic cross-sectional view illustrating usage example 2 of the inosculating section.

The inosculating procedure is performed as below. As shown in FIG. 10A, the line member 40 is slightly fed from the end of the procedure catheter 20b. In the state where the thin line member 40 is slightly projected from the end of the procedure catheter 20b, the line member 40 exhibits extremely high rigidity and functions similarly to a needle. This makes it possible to puncture one of the valve bodies of the mitral valve Mv. After one end of the line member 40 punctures one of the valve bodies of the mitral valve Mv, the line member 40 is fed from the procedure catheter 20b or fractured by the fracture section 41. At this time, as shown in FIG. 10B, the line member 40 self-deforms circularly and the other end of the line member 40 moves toward and punctures the other valve body of the mitral valve Mv. Then, the line member 40 deforms so as to be wound or to make a U-turn. In short, the line member 40 exhibits a loop by itself to thereby function as a clip member 40a which inosculates the mitral orifice O surrounded by a mitral valve Mv, reducing the area of the mitral orifice O small.

Usage Example 2

Figure 12:
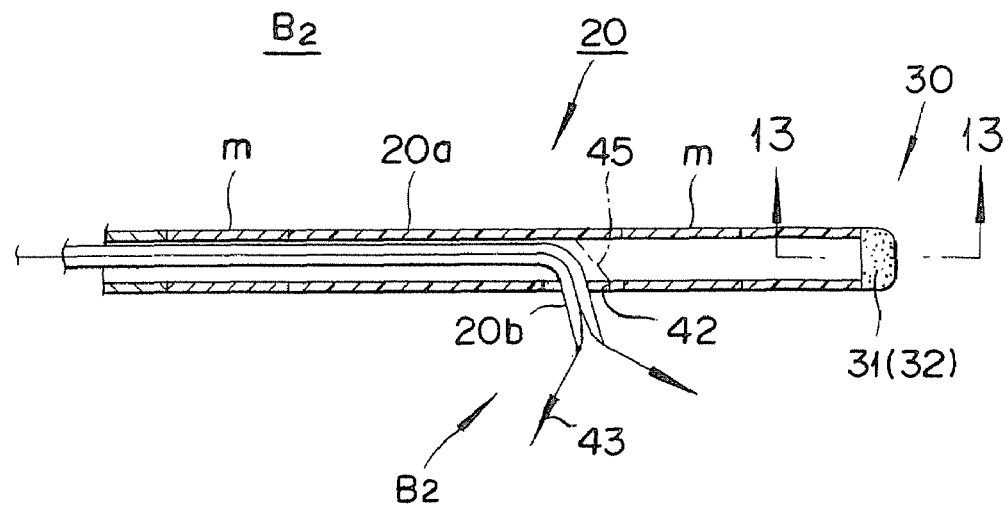
FIG. 12 is an enlarged cross-sectional view of a main portion of FIG. 11.

The inosculating section B2 of usage example 2 is configured as below. A procedure catheter 20b projects from an opening 42 (see FIG. 12) bored at an end portion of a guide catheter 20a. An anchor member 43 provided at an end of the procedure catheter 20b makes a puncture in a mitral valve Mv. Thereafter, the anchor member 43 is made small by the fastening section 49 (see FIG. 15) and released from the procedure catheter 20b. Incidentally, if a guide member 45 (indicated with a chain line) is provided close to the opening 42 of the guide catheter 20a, it is preferred that the procedure catheter 20b easily comes out of the opening 42.

Figure 13A:
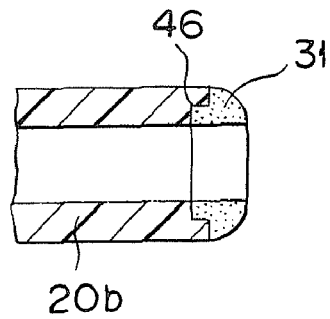
FIGS. 13A and 13B are cross-sectional views taken along line 13-13 of FIG. 12, illustrating a guide catheter provided with adsorption section at its tip.
Figure 13B:
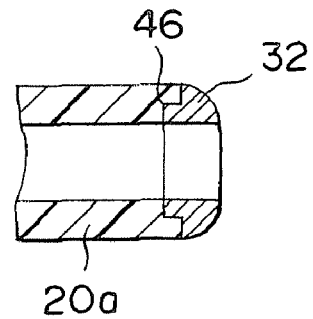

The treatment catheter 20 is not necessarily needed to be installed parallel to the axis of the positioning catheter 10. If the easiness of the procedure or technique is ensured, the treatment catheter 20 may be arranged perpendicularly to the axis of the positioning catheter 10. To provide such arrangement, an adsorption section 30 provided for the guide catheter 20a is preferably configured such that for example a permanent magnet 31 or a to-be-attracted member 32 is provided at the tip of the guide catheter 20a. To attach the permanent magnet 31, as shown in FIG. 13A, a stepped portion 46 may be formed at the tip of the guide catheter 20a and the permanent magnet 31 may be secured to the stepped portion 46 with an adhesive or the like. To attach the to-be-attracted member 32, similarly the to-be-attracted member 32 may be secured to the stepped portion 46 with an adhesive or the like as shown in FIG. 13B.

As described above, the tip of the guide catheter 20a is closed and the procedure catheter 20b provided inside the guide catheter 20a is projected from the lateral side of the guide catheter 20a. This facilitates positioning of the procedure catheter 20b relative to the mitral valve Mv, whereby the procedure is made further reliable and accurate.

Figure 14:
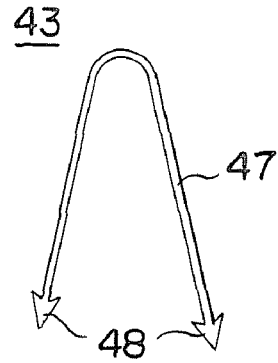
FIG. 14 illustrates an anchor member by way of example.

The inosculating section B2 uses an anchor member 43 which includes an almost-U-bent line member 47 and arrow portions 48 provided at tips of the line member 47, as shown in FIG. 14. The anchor member 43 is attached to fastening section 49 provided at the tip of the procedure catheter 20b. The anchor member 43 is punctured into the mitral valve Mv, and then fastened to be made small, and thereafter released together with the fastening section 49 from the procedure catheter 20b.

Figure 15:
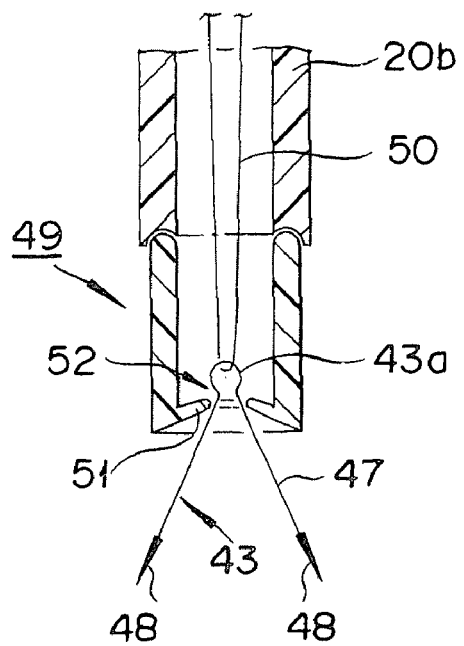
FIG. 15 is an enlarged cross-sectional view of a main portion of fastening section included in the anchor member.

Referring to FIG. 15, the fastening section 49 is configured as below. A turn-up portion 51 is provided at the tip of the procedure catheter 20b and a through-hole 52 is formed at the center of the turn-up portion 51. An arcuate protruding head portion 43a formed in the anchor member 43 is grasped by the inner circumferential portion of the turn-up portion 51. A string like member 50 is joined to the protruding head portion 43a.

Figure 16:
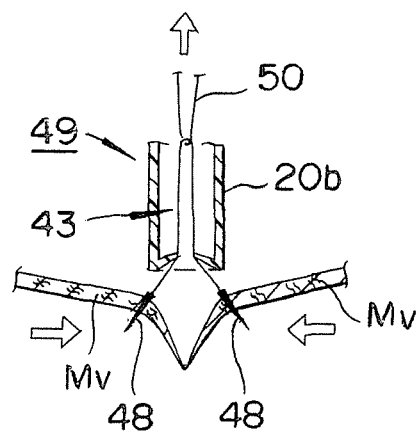
FIG. 16 is a schematic cross-sectional view illustrating a puncturing state of the anchor member.
Figure 17:
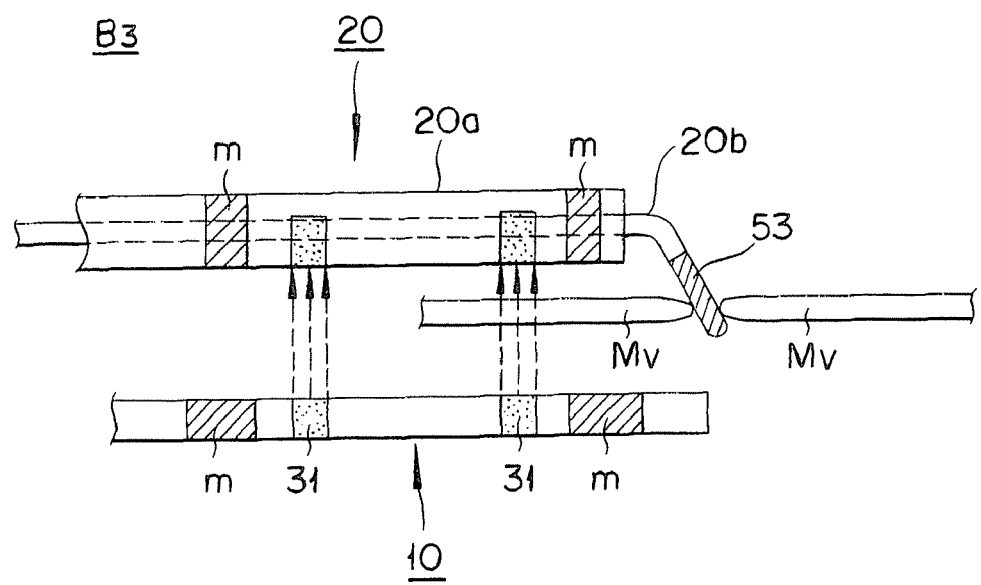
FIG. 17 is a schematic cross-sectional view illustrating usage example 3 of the inosculating section.

The inosculation is performed by the fastening section 49 as below. After the puncture of the anchor member 43, the procedure catheter 20b is pulled axially rearward, whereby the inner circumferential portion of the turn-up portion 51 makes the anchor member 43 small. As shown with outline arrows in FIG. 16, this allows the valve bodies of the mitral valve Mv to be abutted against each other, which reduces the opening area of the opening portion O. When the procedure catheter 20b is further pulled rearward, the stringlike member 50 is overcome by the state of the engagement between the anchor member 43 and the mitral valve Mv to fracture or to be withdrawn. Consequently, the anchor member 43 and the fastening section 49 are released from the procedure catheter 20b.

If the fastening section 49 is used for the puncture as described, the arrow portions 48 of the anchor member 43 puncture both the valve bodies of the mitral valve Mv at the same time. After the puncture, if the procedure catheter 20b is pulled rearward, the anchor member 43 can be implanted on the mitral valve Mv, which makes the procedure easy.

In particular, when the anchor member 43 punctures the mitral valve Mv, the puncture force direction of the anchor member 43 may be coincident with the attractive force direction of the to-be-attracted members 32 of the guide catheter 20a depending on the procedure or puncture position. The adsorption section 30 directly assists the puncture of the anchor member 43, which makes the procedure extremely smooth.

Usage Example 3

The inosculating section described above uses the clip member 40a or the anchor member 43 to make the mitral orifice O surrounded by a mitral valve Mv small. The present usage example uses a fusion member 53 to perform fusion or thermocoagulation through electric section.

The inosculating section B3 is configured to include a fusion member 53, specifically an RF (radio frequency) electrode, provided at the tip of a procedure catheter 20b. The fusion member 53 of the procedure catheter 20b is inserted between the valve bodies of a mitral valve Mv. Radio-frequency current is then applied from external control section (not shown) to the fusion member for heating while controlling the temperature of the RF electrode. Thus, the tissues of both the valve bodies of the mitral valve Mv are heat-sealed or heat-coagulated for joining.

Preferably, also the fusion member 53 is made of a shape memory alloy. At first the fusion member 53 is linear when located inside the guide catheter 20a. This makes it easy for the fusion member 53 to move inside the guide catheter 20a. When the fusion member 53 reaches the mitral valve Mv, it bends at a predetermined angle and is easily inserted between the valve bodies of the mitral valve Mv. Thus, the use of the memory shape alloy can make the procedure smooth and is preferable in view of operability.

Incidentally, the fusion member 53 can use e.g. ultrasonic sound, laser, microwaves or the like as an energy source. A gripping member may be provided near the RF electrode to enable the constant application of a press-fitting force to the tissue contracted by the heating.

A description is next made of the function of the embodiment of the present invention.

At first, an operator inserts a guide wire (not shown) into a living body, passes the positioning catheter 10 through the living body using the guide wire as a guide and inserts it into the coronary vein 11 of the heart. When the positioning catheter 10 reaches the vicinity of the mitral valve Mv, it is maintained at the position.

Next, the operator inserts a guide wire (not shown) into the living body from an inferior vena cava J (see FIG. 1). The operator passes the treatment catheter 20 through the living body using the guide wire as a guide, inserts it from the right atrium R of the heart through a valve-like portion (not shown) of a membrane S between the right atrium R and the left ventricle L and delivers it to the position of the mitral valve Mv.

Incidentally, the insertion of the catheters 10, 20 can be performed while confirming the positions of the markers m with X-ray irradiation or the like; therefore, the positions of the catheters 10, 20 in the living body can accurately be grasped.

The treatment catheter 20 is attracted to an appropriate position by the adsorption section 20 of the positioning catheter that has preliminarily been inserted. Thus, although under the condition where the heart H acts to pump a quantity of blood, the treatment catheter 20 does not float but can be held position-fixedly.

In other words, the thin positioning catheter 10 that is easily inserted into the heart H is used, inserted into a relatively narrow portion or the coronary vein 11 and brought into an immovable state. The treatment catheter 20 that is similarly easily inserted into the heart H is fixed in position by using the positioning catheter 11. Although in blood, the floating of the treatment catheter 20 is restricted by the positioning catheter 10. Thus, the procedure by the treatment catheter 20 is significantly simplified and becomes accurate.

In addition, if the treatment catheter 20 holding the inosculating section B is positionally fixed, the direction of force adapted to insert the inosculating section B into the valve body may be coincident with the direction of attracting force of the adsorption section 30. Thus, the adsorption section 30 will exhibit a large assistant force for the procedure.

When the procedure catheter 20b projects from the tip of the treatment catheter 20, the guide wire is withdrawn and the inosculating section B inserted into the procedure catheter 20b is operated to start the procedure.

For example, for the inosculating section B1, the line member 40 is allowed to project from the tip of the procedure catheter 20b and operated to puncture both the valve bodies of the mitral valve Mv. After the puncture, the line member 40 comes into a wound state by itself to move toward the other valve body for puncture. After the confirmation of the puncture, the line member 40 is fractured by the fracture section 41 to come into a loop state by itself, functioning as the clip member 40a to inosculate the mitral orifice O surrounded by a mitral valve Mv, thereby reducing its area of the mitral orifice O. Incidentally, if the line member 40 is fed every predetermined length without fracture, it is preferred that the line member be fed gradually while confirming the puncture to the other valve body of the mitral valve Mv.

For the inosculating section B2, the procedure catheter 20b is allowed to project from the opening 42 bored at the leading end portion of the guide catheter 20a. The anchor member 43 provided at the tip of the procedure catheter 20b punctures the mitral valve Mv and then is fastened by the fastening section for inosculation.

For the inosculating section B3, the fusion member 53 provided at the tip of the procedure catheter 20b is inserted between the valve bodies of the mitral valve Mv. Radio-frequency current is then applied from the external control section to the mitral valve Mv for heating while controlling the temperature of the RF electrode. Thus, the tissues of both the valve bodies of the mitral valve Mv are heat-sealed or heat-coagulated for joining.

After the procedure is completed as described above, the procedure catheter 20b is moved backward in the guide catheter 20a to withdraw the entire treatment catheter 20 from the living body and also the positioning catheter 10 is withdrawn from the living body.

The present invention is not limited to the embodiments described above but can be modified or altered in various ways by those skilled in the art in the scope of the technical concept of the invention. For example, the embodiments described above can be used to cure the mitral valve Mv but the invention is not limited to this. The invention can be used for the case where the closing conditions of various valve bodies such as an aortic valve are poor, or for the cure not only for the heart but also for a portion where a relatively thick blood vessel exists close to an affected region.

The present invention can be used as a medical device that can inosculate the opening portion of a mitral valve simply and safely.

While preferred embodiments of the present invention have been described using specific terms, such description is for illustrative purposes, and it is to be understood that changes and variations may be made without departing from the spirit or scope of the following claims.

What is claimed is:

1. A medical device comprising:
a positioning catheter configured to be inserted into a coronary vein or a coronary artery in the vicinity of an affected region in the left atrium;
a treatment catheter configured to be inserted to reach the affected region in the left atrium;
attracting means provided at respective predetermined positions of both the catheters to apply a magnetic force in a direction of attracting each other;
wherein the magnetic force of the attracting means restricts floating of the treatment catheter;
wherein the attracting means includes magnets provided at any one of the positioning catheter and the treatment catheter and to-be-attracted members provided on the other of the catheters, and
the magnets are provided at a leading end portion of any one of the catheters at two or more positions so as to be axially spaced apart from each other and the to-be-attracted members are provided at an leading end portion of the other of the catheters at two or more positions so as to be axially spaced apart from each other.

2. The medical device according to claim 1, wherein the positioning catheter and the treatment catheter are each provided with a marker at the leading end thereof.

3. The medical device according to claim 2, wherein the treatment catheter includes a guide catheter and a procedure catheter inserted into the guide catheter and having inosculating means at a tip thereof.

4. The medical device according to claim 1, wherein the treatment catheter includes a guide catheter and a procedure catheter inserted into the guide catheter and having inosculating means at a tip thereof.

5. The medical device according to claim 4, wherein the treatment catheter is configured such that the guide catheter is provided at a leading end thereof with the attracting means which applies a magnetic force in a direction of attracting the positioning catheter.

6. The medical device according to claim 5, wherein the inosculating means is a clip member which is formed of a thin line member made of a shape memory alloy with a predetermined length and which is configured to puncture the affected region and deform to narrow an opening portion of the affected region.

7. The medical device according to claim 5,
wherein the inosculating means includes:
an anchor member which is made of a U-shaped line member to be formed with arrow portions at tips thereof and which punctures the affected region to narrow the opening portion of the affected region; and
fastening means adapted to release the anchor member from the treatment catheter.

8. The medical device according to claim 5,
wherein the inosculating means includes:
a fusion member which is inserted into the opening portion of the affected region to narrow the opening portion through thermal fusion bond; and
controlling means for controlling the temperature of the fusion member.

9. The medical device according to claim 4, wherein the inosculating means is a clip member which is formed of a thin line member made of a shape memory alloy with a predetermined length and which is configured to puncture the affected region and deform to narrow an opening portion of the affected region.

10. The medical device according to claim 4,
wherein the inosculating means includes:
an anchor member which is made of a U-shaped line member to be formed with arrow portions at tips thereof and which punctures the affected region to narrow the opening portion of the affected region; and
fastening means adapted to release the anchor member from the treatment catheter.

11. The medical device according to claim 1, wherein the positioning catheter and the treatment catheter are each provided with a marker at the leading end thereof.

12. The medical device according to claim 1, wherein the treatment catheter includes a guide catheter and a procedure catheter inserted into the guide catheter and having inosculating means at a tip thereof.

13. A medical device according to claim 1, wherein the medical device is specifically configured to narrow an opening portion of a mitral valve.

14. A medical device comprising:
a positioning catheter configured to be inserted into a coronary vein or a coronary artery in the vicinity of an affected region in the left atrium;
a treatment catheter configured to be inserted to reach the affected region in the left atrium;
attracting means provided at respective predetermined positions of both the catheters to apply a magnetic force in a direction of attracting each other;
wherein the magnetic force of the attracting means restricts floating of the treatment catheter; and
wherein the attracting means comprises a plurality of axially spaced apart magnets fixed to one of the positioning catheter and the treatment catheter, and a plurality of axially spaced apart to-be-magnetically attracted members fixed to the other of the positioning catheter and the treatment catheter.

15. A medical device comprising:
a positioning catheter to be inserted into a blood vessel in the vicinity of an affected region;
a treatment catheter to be inserted to reach the affected region; and
axially spaced apart magnets provided at a leading end of one of the positioning catheter and the treatment catheter, and axially spaced apart to-be-attracted members provided on the other of the positioning catheter and the treatment catheter to apply a magnetic force in a direction of attracting each other, the magnetic force of the attracting means restricting floating of the treatment catheter.

* * * * *